US006490039B2

(12) United States Patent
Maleki et al.

(10) Patent No.: US 6,490,039 B2
(45) Date of Patent: Dec. 3, 2002

(54) OPTICAL SENSING BASED ON WHISPERING-GALLERY-MODE MICROCAVITY

(75) Inventors: Luftollah Maleki, Pasadena; Vladimir Ilchenko, La Canada, both of CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 09/925,713

(22) Filed: Aug. 8, 2001

(65) Prior Publication Data

US 2002/0097401 A1 Jul. 25, 2002

Related U.S. Application Data

(60) Provisional application No. 60/223,673, filed on Aug. 8, 2000, provisional application No. 60/278,967, filed on Mar. 26, 2001, and provisional application No. 60/292,200, filed on May 18, 2001.

(51) Int. Cl.[7] .............. G01N 21/00; H01S 3/08; G02B 6/26

(52) U.S. Cl. .............. 356/436; 356/440; 356/442; 385/28; 385/30; 372/98; 372/108

(58) Field of Search .................... 356/436, 440, 356/442; 385/28, 30; 372/98, 108

(56) References Cited

U.S. PATENT DOCUMENTS

5,742,633 A     4/1998  Stone et al.

OTHER PUBLICATIONS

Rosenberger et al., "Evanescent–wave sensor using microsphere whispering–gallery modes," *Laser Resonators III*, Proceedings of SPIE, vol. 3930, pp 186–192, 2000.

Blair et al., "Resonant–enhanced evanescent–wave fluorescence biosensing with cylindrical optical cavities," Allied Optics, vol. 40, No. 4, pp. 570–582, Feb. 1, 2001.

*Primary Examiner*—Frank G. Font
*Assistant Examiner*—Roy M. Punnoose
(74) *Attorney, Agent, or Firm*—Fish & Richardson, P.C.

(57) ABSTRACT

Techniques and devices for sensing a sample by using a whispering gallery mode resonator.

28 Claims, 6 Drawing Sheets

OPTICAL SENSING BASED ON WHISPERING-GALLERY-MODE MICROCAVITY

This application claims the benefits of U.S. Provisional Application No. 60/223,673 entitled "Microcavity Sensor" and filed on Aug. 8, 2000, No. 60/278,967 entitled "Enhanced Micro-Cavity Sensor for Biochemical and Biomedical Applications" and filed on Mar. 26, 2001, and No. 60/292,200 entitled "Devices Based on Whispering Gallery Mode Resonance" and filed on May 18, 2001.

ORIGIN OF THE INVENTION

The systems and techniques described herein were made in the performance of work under a NASA contract, and are subject to the provisions of Public Law 96-517 (35 USC 202) in which the Contractor has elected to retain title.

BACKGROUND

This application relates to techniques and devices for optical sensing and optical detection.

Optical sensing generally uses an optical probe beam to interact with a material to be detected. This interaction between the optical probe beam and the material modifies some aspect of the optical probe beam. A portion of this modified beam, such as the scattered light, the reflected light, or the transmitted light, may be collected and measured to obtain certain information of the material. For example, the optical intensity, phase, spectrum, polarization, or direction of the collected light may be measured either individually or in combination with other parameters to determine the certain information of the material.

Optical sensing may be used to achieve a number of advantages. For example, the sensing can be non-invasive and does not alter the material to be measured under proper operating conditions. The spectrum of the probe beam may be controlled to selectively interact with only certain optical transitions in specified particles, molecules, or atoms in the material. Optical sensing may also be used to achieve high detection sensitivity and to detect minute amount of a particular material.

SUMMARY

This disclosure includes optical sensing techniques and devices based on whispering-gallery-mode micro resonators or cavities. An optical probe beam is evanescently coupled into at least one whispering gallery mode of such a resonator. A sample material to be measured may be filled within the resonator or surrounded outside the resonator to interact with and modify the whispering gallery mode or geometry of the resonator. The evanescent field outside the resonator is detected or measured to detect a change caused by the modification. This change is then processed to extract information about the sample material. This change may be reflected as, e.g., a temporal change in the mode structure during a transient period, attenuation in the evanescent field, a frequency shift in the whispering gallery mode and its evanescent field, or a change in efficiency of the evanescent coupling of the probe beam into the resonator or coupling of the energy in the whispering gallery mode out of the resonator.

In one implementation, the quality factor of the resonator for a particular mode may be measured to extract the information about the sample material by, e.g., measuring the spectral bandwidth of the mode or decay time of the mode. In he another implementation, the frequency shift is measured. In yet another implementation, the intensity of light coupled out of the resonator is measured. The resonator may also be actively controlled, e.g., by using a control signal to adjust its dimension, this control signal required to maintain certain desired conditions can be measured before and after the sample is introduced. The change in the control signal, e.g., its magnitude, may be used to extract information on the sample.

DETAILED DESCRIPTION

Figure 1A:
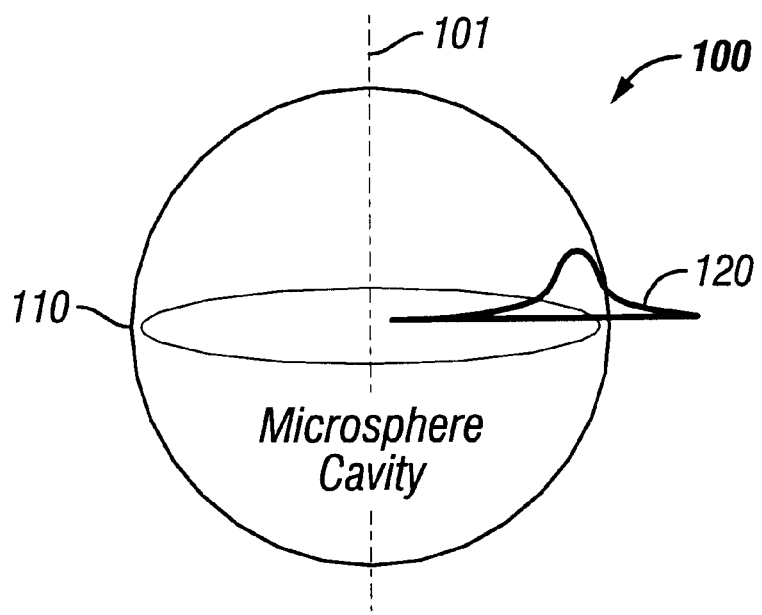
FIG. 1A shows a microsphere whispering-gallery-mode cavity to illustrate the general operations of whispering-gallery-mode cavities and two-dimensional curvature confinement.

FIG. 1A shows one embodiment 100 of a micro whispering-gallery-mode resonator formed of a dielectric sphere with a symmetric axis 101. The micro resonator 100 generally may be formed from at least a portion of a whole dielectric sphere that includes the equator 110 of the sphere. Such a spherical resonator can support a special set of resonator modes known as "whispering gallery modes" which are essentially electromagnetic field modes confined in an interior region close to the surface of the sphere around its equator 110 and circulating by total internal reflection inside the axially symmetric dielectric body. Microresonators, such as microspheres, with dimensions on the order of $10 \sim 10^2$ microns have been used to form compact optical resonators. Such resonators have a resonator dimension much larger than the wavelength of light so that the optical loss due to the finite curvature of the resonators can be small. The primary sources for optical loss include optical absorption in the dielectric material and optical scattering due to the inhomogeneity of the sphere (e.g., irregularities on the sphere surface). As a result, a high quality factor, Q, may be achieved in such resonators. Some microspheres with sub-millimeter dimensions have been demonstrated to exhibit very high quality factors for light waves, exceeding $10^9$ for quartz microspheres. Hence, optical energy, once coupled into a whispering gallery mode, can circulate at or near the sphere equator with a long cavity storage time. The resonator 100 may be the whole sphere or a portion of the sphere near the equator 110 that is sufficiently large to support the whispering gallery modes such as rings, disks and other geometries.

The very high quality factors Q of microspheres may be attributed to several factors. One factor is that the dielectric materials for microspheres are selected to have ultra-low optical loss at the frequencies of the supported whispering gallery modes. Fiber-grade fused silica may be used for resonators operating at wavelengths near 1.3 and 1.5 microns at which the optical loss is low. Another factor is that the surface of the sphere is specially fabricated to minimize the size of any surface inhomogeneities, e.g., on the order of a few Angstroms by processes such as fire polishing. The high index contrast in microsphere cavities is also used for steep reduction of radiative and scattering losses with increasing radius. In particular, microspheres have a curved circumferential edges above and below their equators to provide a two-dimensional curvature confinement to the optical energy in a WGM for grazing reflection of all wave vector components. This grazing incidence in a sphere can be essential for minimizing surface scattering that would otherwise limit the Q far below that imposed by attenuation in the material. For example, in the integrated optical micro-ring and micro-disk cavities based on planar waveguide technology, the ring and disks are formed from cylinders with straight side walls. As a result, the light is confined only by a curved geometry along one dimension and effectively bounces from flat surfaces under finite angles. Hence, typical Q-factor of such cavities is limited to about $10^4 \sim 10^5$.

Spherical cavities including at least a portion of a sphere with its equator are only one type of microcavities that provide two-dimensional curvature confinement for achieving high Q values. Notably, the micro resonator suitable for the present sensing applications may also have non-spherical resonator geometries that are axially symmetric. Such a non-spherical resonator may be designed to retain the two-dimensional curvature confinement, low scattering loss, and very high Q values of typical spherical resonators (spheres, disks, rings, etc.). In one embodiment, instead of minimizing the eccentricity, such a non-spherical resonator may be formed by distorting a sphere to a non-spherical geometry to purposely achieve a large eccentricity, e.g., greater than $10^{-1}$. U.S. patent application Ser. No. 09/816,872, entitled "NON-SPHERICAL WHISPERING-GALLERY-MODE MICROCAVITY" and filed Mar. 22, 2001 by Maleki et al., for example, describes an oblate spheroidal microcavity or microtorus formed by revolving an ellipse around a symmetric axis along the short elliptical axis.

Such non-spherical microcavities have different WGM structures from the spherical counterparts although both have high Q values. The spherical cavities have a relatively dense spectrum of modes. In an ideal sphere with zero eccentricity, the optical spectrum of the sphere has TE(TM)$_{lmq}$ modes separated by a free spectral range (FSR) defined by the circumference of the sphere and related to consecutive values of the mode index l. The mode index l approximately represent the number of wavelengths that fit into the optical length of the equator, m the number of field maxima in the equator plane, and q the field maxima in the direction along the radius in the equator plane.

Each of TE(TM)$_{lmq}$ modes, however, is degenerate and includes (2l+1) modes given by the possible values of the mode index m. In actual spheres, the spherical surfaces are usually not perfectly spherical and have residual nonsphericity. This deviation from the perfect spherical surface lifts the mode degeneracy and breaks down each TE(TM)$_{lmq}$ mode with a given value for the mode index l into a series of observable TE(TM)$_{lmq}$ modes with different values in the mode index m under each value for the mode index l. Therefore, a nonideal spherical resonator exhibits two different values for the free spectral range (FSR): a "large" FSR which is the frequency spacing between two adjacent TE(TM)$_{lmq}$ modes with the same values for indices m and q but with a difference of 1 in their l values, and a "small" FSR which is the frequency spacing between two adjacent TE(TM)$_{lmq}$ modes with the same l values but with a difference of 1 in their m values:

"Small" FSR:

$$v_{lmq} - v_{l,m-1,q} \sim v \frac{\varepsilon^2}{2l}$$

"Large" FSR:

$$v_{lmq} - v_{l-1,mq} = \frac{c}{2\pi na}(t_{lq} - t_{l-1,q}) \sim v/l$$

In silica spheres of diameters of about 150 to 400 microns, for example, typical fabrication techniques usually produce an eccentricity of about $\varepsilon^2 = 3 \times 10^{-2}$. The "large" FSR may be in the range of 437 to 165 GHz, or in the wavelength scale, 3.5 to 1.3 nm near the center wavelength 1550 nm. The "small" FSR may be in the range of 6.8–2.5 GHz. As a result, even though the spheres are capable of producing a large FSR on the order of hundreds of GHz, the actual spectrum of such spheres are relatively dense with a useful FSR limited by the "small" FSR typically under 10 GHz.

The above relatively dense spectrum in a typical sphere resonator may limit applications of the resonator since it can complicate spectral analysis, especially in the data processing for sensing applications as described in the present application. In addition, intermediate filtering may be needed to eliminate some of the modes to obtain a spectrum with well-separated resonance peaks.

Hence, one way to achieve a FSR on the order of hundreds of GHz in spherical resonators without external spectral filtering is to maintain the mode degeneracy so that the "large" FSR in the whisper gallery modes TE(TM)$_{lmq}$ for given values in the mode index l can be produced in the resonator's spectrum. Under this approach, the eccentricity of the sphere should be minimized.

Figure 1B:
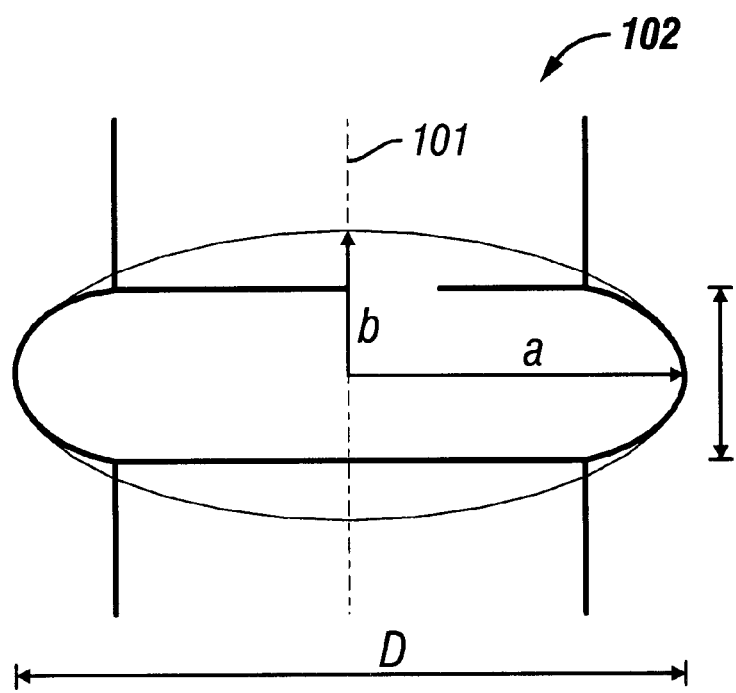
FIG. 1B shows an oblate spheroidal microcavity as an example of non-spherical geometries that provide for two-dimensional curvature confinement.

Alternatively, non-spherical resonator geometries formed by distorting a sphere to a non-spherical geometry to purposely achieve a large eccentricity, e.g., greater than $10^{-1}$. FIG. 1B shows an oblate spheroidal microcavity or microtorus as one example of such non-spherical microcavities.

FIG. 1B shows one embodiment of a spheriodal microcavity 101 formed of an optical dielectric material. The cavity 100 is formed by revolving an ellipse around a symmetric axis along the short elliptical axis 101. The lengths of the long and short elliptical axes are a and b, respectively. Hence, the eccentricity of cavity 100 is $\varepsilon^2 = (1 - b^2/a^2)$. Near the symmetry plane at the location of WG modes, toroidal surface of outer diameter D and cross-section diameter d coincides with that of the osculating oblate spheroid with large semiaxis a=D/2 and small semi-axis b=½√Dd. The dimension D of the spheroid 100 may be less than 10 mm for operations in the optical and microwave spectral ranges. The eccentricity may be greater than 0.5.

In both spherical and non-spherical micro resonators with two-dimensional curvature confinement, the central portion of the resonators may be removed to have a hollow central region. Such a ring-like spherical or spheroidal configurations can support the WGMs as long as a sufficient volume remains near the equator to contain the WGM.

Optical energy can be coupled into the above resonators by evanescent coupling, e.g., using an optical coupler near the resonator 100 or 102 by less than one wavelength of the optical radiation to be coupled. Although a whispering gallery mode confined within the resonator 100 or 102, its evanescent field 120 "leaks" outside the resonator 100 or 102 within a distance about one wavelength of the optical signal, the extent of evanescent wavelength propagation being dependent on the mismatch of refractive indices of the resonator material and surrounding medium. The optical coupler may have a receiving terminal to receive an input optical wave at a selected wavelength and a coupling terminal to evanescently couple the optical wave into the resonator 100 or 102. In addition, the optical coupler may also be used to couple the optical energy in one or more whispering gallery modes out of the resonator 100 to produce an optical output. The output may be coupled to an optical detector to convert the information into electronic form or an optical device or system for photonic processing, optical storage, or optical transmission such as a fiber link. The input optical beam may be generated from a light source such as a laser.

Figure 2:
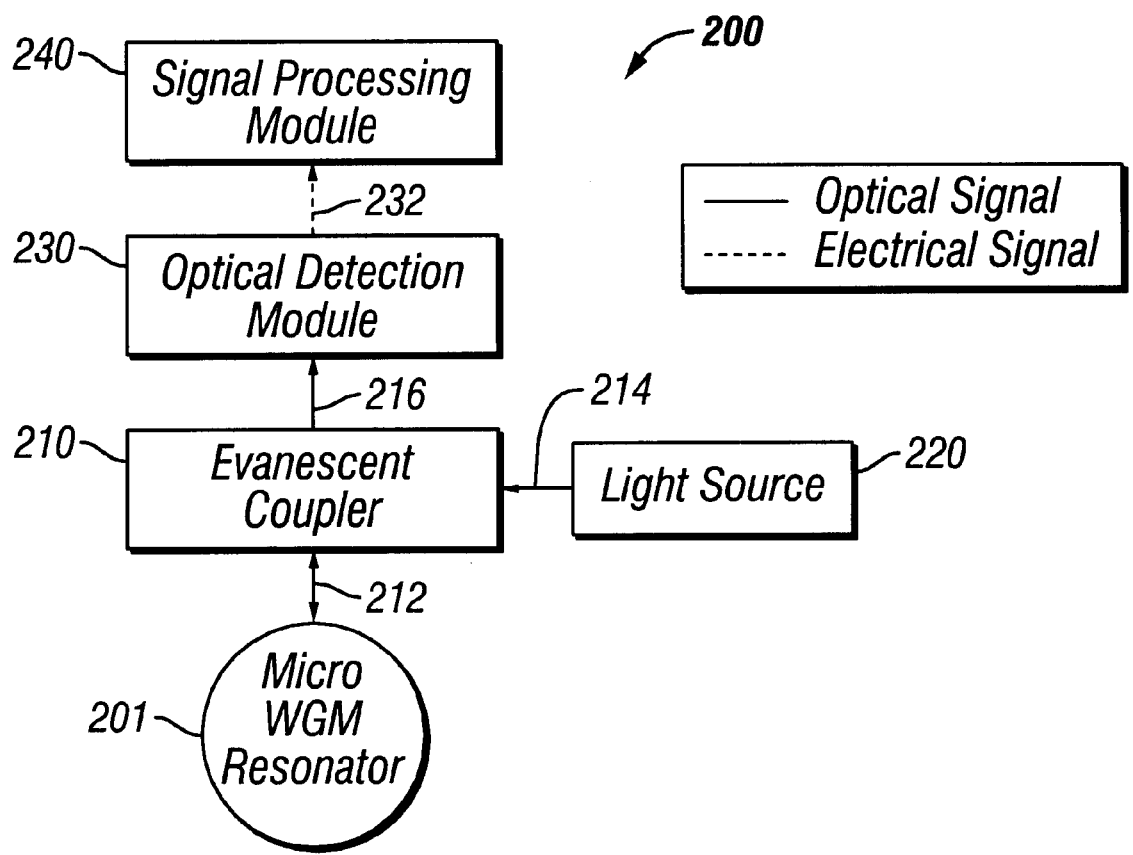
FIG. 2 shows an optical sensing device by using a whispering-gallery-mode (WGM) cavity according to one embodiment.

FIG. 2 shows one embodiment of an optical sensing device 200 by using a micro WGM resonator 201. An evanescent coupler 210 is used to couple an input beam 214 from a light source 220 to the resonator 201 via an evanescent field 212. The coupler 210 may also couple energy out of the resonator 201 to produce an output optical signal 216. An optical detection module 230 is used to receive and detect the signal 216 to produce a detector signal 232. A signal processing module 240 processes the signal 232 to produce the desired measurement of the sample. The processing module 240 may include a microprocessor to process and infer the desired property of the sample from the information in the detector signal 232.

Figure 3A:
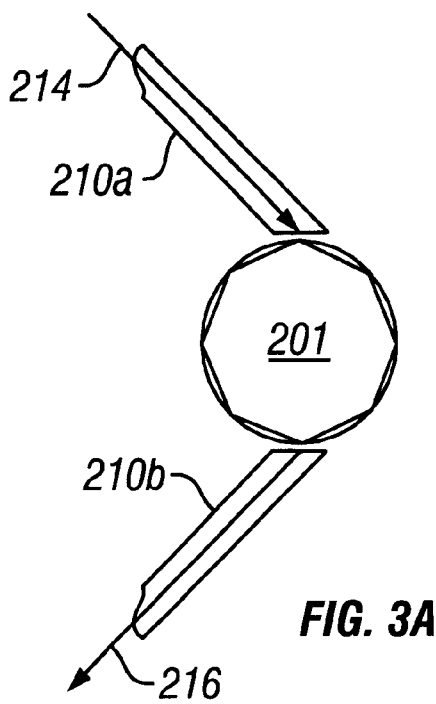
FIGS. 3A, 3B, 3C, and 3D show exemplary evanescent coupling schemes that may be used in the optical sensing device in FIG. 2.
Figure 3B:
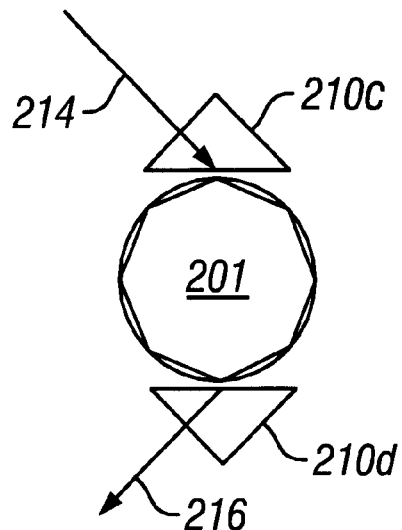
Figure 3C:
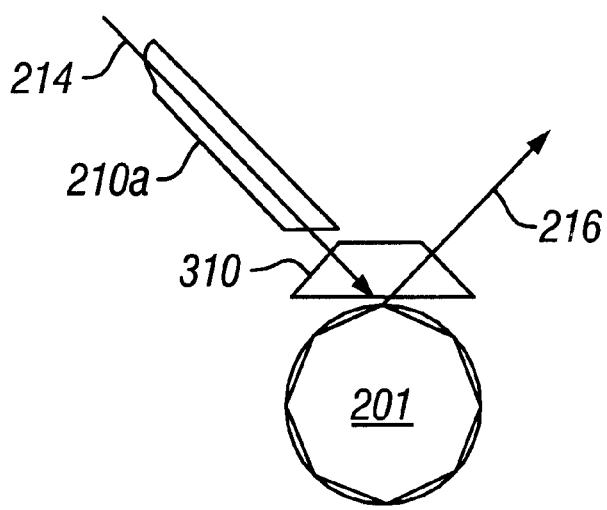
Figure 3D:
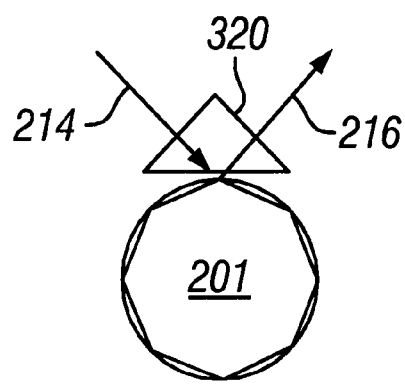

In one embodiment, the evanescent coupler 210 may be implemented by using one or two angle-polished fibers or waveguides 210A and 210B as shown in FIG. 3A. Such fibers or waveguides are generally designed to support a single mode. The angle-polished tip is placed near the resonator 201 to effectuate the evanescent coupling. The index of refraction of the fibers or waveguides 210A and 210B is greater than that of the resonator 201, and the optimal angle of the polish has to be chosen depending on the ratio of indices. See, e.g., V. S. Ilchenko, X. S. Yao, L. Maleki, Optics Letters, Vol.24, 723(1999). In another embodiment, evanescent coupler 210 may be implemented by using one or two micro prisms 210C and 210D as shown in FIG. 3B. A single angle-polished waveguide or fiber, or a single micro prism 310 or 320 may be used to operate as the evanescent coupler 210 to couple both the input wave 214 and the output wave 216 as shown in FIGS. 3C and 3D. An angle-polished fiber can also be used without assistance of a prism to for both input and output coupling.

Independent of its physical realization, the coupler 210 may be coated with a material sensitive to presence of analyte in solution surrounding the microresonator. The coupling efficiency and mode structure would then be dependent on the presence of the analyte in solution.

Figure 4:
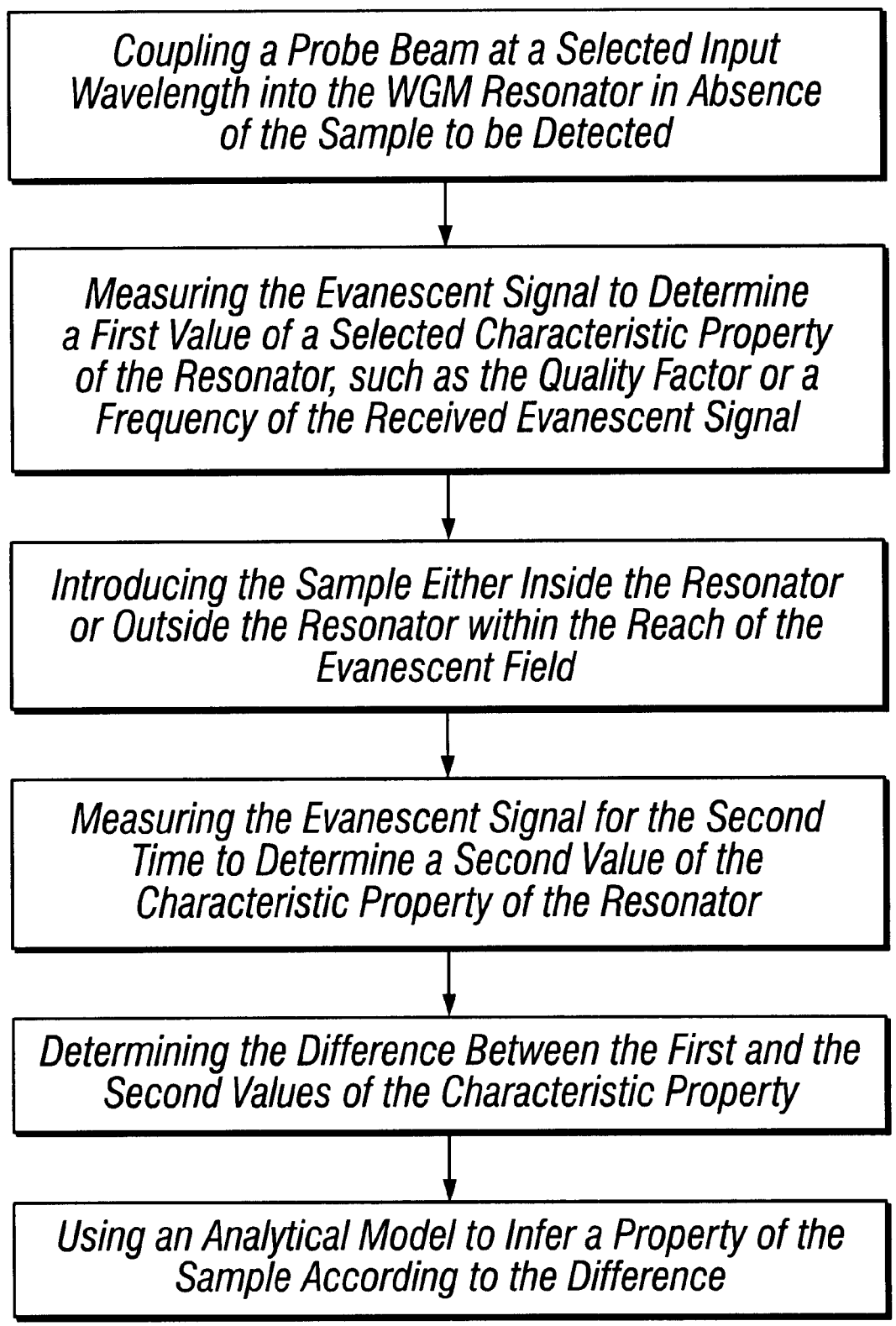
FIG. 4 shows one exemplary flow for measuring a sample by a WGM cavity.

The basic operation of the device 200 is illustrated by the flowchart in FIG. 4 according to one embodiment. A sample to be measured, usually a minute quantity of sample particles, is introduced to be present in the reach of WGM field of the resonator 201. Because the WGM fields are present both within and outside the resonator 201, the sample may also be introduced either within the resonator 201 or outside the resonator 201. Various techniques for introducing the sample will be described. However introduced, the sample can interact with the WGM field to produce a change in the output signal 216 when compared to the output signal 216 in absence of the sample. This change, therefore, can be used to extract information on a desired property of the sample.

Figure 5A:
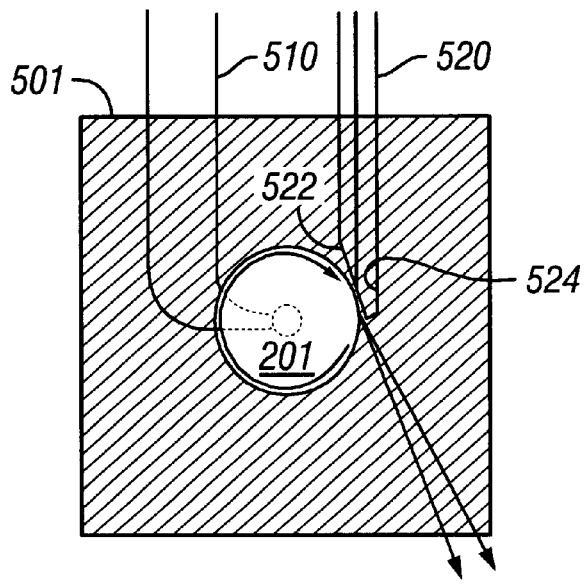
FIGS. 5A, 5B, 6A, and 6B show two different ways of introducing a sample to the WGM cavity for measurement.
Figure 5B:
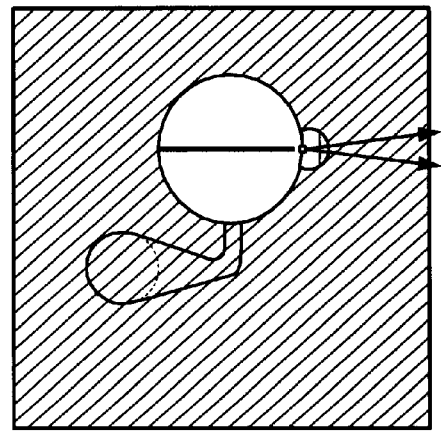

FIGS. 5A and 5B show one implementation where the resonator 201 is a solid dielectric body (such as a sphere) and the sample is introduced in the surrounding area of the resonator 201. A sample chamber 501 is provided to enclose the resonator 201 and the sample. A resonator holder 510 is used to hold the resonator 201 and to place it at a desired location in the sample chamber 501. The sample chamber 501 may be filled with a gaseous or liquid medium in which the sample will be added. The refractive index of the dielectric material of the resonator 201 is higher than that of the medium in the sample chamber 501. Referring to the operation shown in FIG. 4, the medium in the sample chamber 501 is initially free of the sample and the output evanescent signal 216 of the resonator 201 is measured. Next, the sample is introduced into the chamber 501 to reach the surface of the resonator 201. The output signal 216 is measured again and is compared to the initial measurement. The difference in the measured signals is processed to determine the property of the sample.

A fiber 520 is shown to operate as an input and output coupler without a prism. The tip of the fiber 520 is angle-polished to form an angled surface 522 for evanescent coupling. The tip is further polished to form a second surface 524 to output the reflected light from the polished surface 522 within the fiber 520. The output signal 216 is thus exported from the fiber 520 through the second polished surface 524.

As long as the surrounding medium has smaller refractive index than the sphere material, the WG microcavity sensing can be performed in condensed media. Glass microcavities can be immersed in water and important organic solvents (methanol, ethanol, acetone and others) without destroying conditions for WG modes. Because of small intrinsic losses in these fluids (typically in the approximate rang of $10^{-3}$~$10^{-1}$ cm$^{-1}$ in the visible spectral range up to near-infrared), the high Q in the approximate range of $10^7$–$10^9$ is preserved. Measurements of changes to the resonator can be used for detection small amount of dissolved absorptive species. Such measurements may include, for example, added losses, manifested in reduction of Q, reduction of the intensity of the coupled light, change in the optical frequency, a change in an applied electric signal to alter the index of refraction of the cavity or the coupling mechanism, or a temporal change in the mode spectrum during a transient period after the sample is introduced. Based on spectroscopic profile of added attenuation and/or reference sample calibration, small amounts of analytes under investigation can be identified and their concentration can be measured.

Figure 6A:
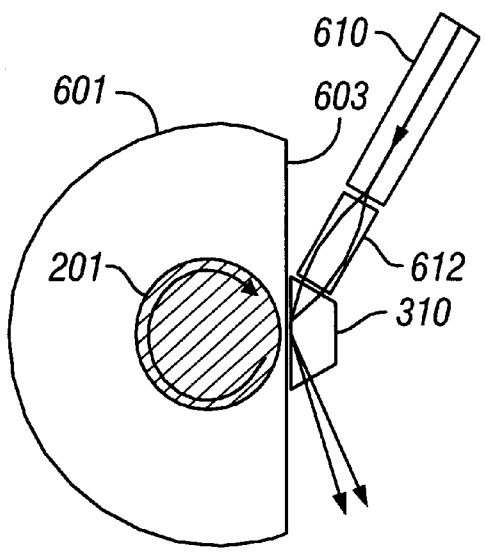
Figure 6B:
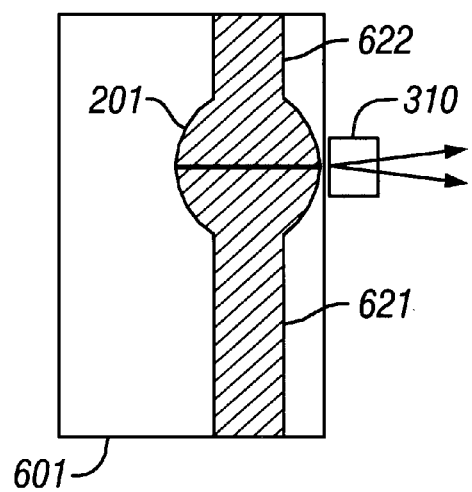

Alternatively, FIGS. 6A and 6B show a hollow WGM resonator formed of a dielectric material with an index less than or equal to that of the medium to be filled therein. The thickness of the resonator wall should be less than one wavelength of the light so that the evanescent coupling is possible. In general, the medium that fills in the hollow chamber of the resonator 201 is a high-index liquid. FIG. 6B also shows that, the chamber of the resonator 201 is connected to tubes 621 and 622 for conducting the fluid. Similar to the operation of the sensing device shown in FIGS. 5A and 5B, the evanescent output signal is measured twice, one measurement without the sample in the fluid and another measure without the sample in the fluid. A cavity holding apparatus 601 is provided to support the resonator 201 and the tubes 621, 622. The apparatus 601 also provides an optical surface 603 spaced from the resonator 210 by a distance less than one wavelength to "tunnel" the evanescent light out of the resonator 201. A prism 310 is used to direct the output light to the optical detection module. FIG. 6A also shows that, a fiber 610 and a collimator 612 (e.g., a GRIN lens) may be used to couple the input light into the prism 310. Hollow spheroid microresonators may also be used in a similar way to form a sensing system.

The influence of the sample on the resonator may be measured in a number of techniques or in a combination of such techniques. One example is the quality factor, Q, as for any resonator. In addition, the cavity has a mode structure, similar to any other resonant cavity. Once light is coupled into a WGM microcavity, the WG modes circulate in the resonator and produce an evanescent wave that protrudes from the surface into the surrounding medium. The evanescent wave decays with a length that is related to the ratio of the index of refraction of the sphere and the surrounding medium, and is typically on the order of, e.g., $0.5\mu$. The microsphere material is transparent at the wavelength of the WG modes and can be glass, quartz or plastics such as polystyrene or polycarbonate. One suitable material may be selected according to the specific requirements of a particular application.

Since the evanescent wave extends beyond the microcavity surface, it samples the surrounding medium and experiences losses due to absorption or other light attenuation casued by the surrounding medium. In the case where the sample is introduced inside a hollow microcavity, the evanescent wave extending outside the cavity surface also reflects the change in Q by the sample. This change in Q thus can be used as a sensing technique for measing gases, liquids, or solids. Interactions of the evanescent wave at the surface and surrounding medium determine Q and the mode structure. The evanescent wave circulates in a small band around the microcavity that is a few tens of micron tall. For a glass sphere in methanol, for example, the evanescent wave penetrates approximately 100 nm in the medium, so the sampled volume is about $2.8 \times 10^{-10}$ liter.

A number of mechanisms based on monitoring optical attenuation or subtle changes in the refractive index may be utilized to detect the presence of a substance producing these changes. These include atoms and molecules with chemical or biological origin. For example, as an analyte interacts with the surface, it causes a change in the mode structure (i.e. light storage properties) due to a change in the index of refraction, or light coupling strength, or change in the geometric size of the optical resonator. If the surface can be treated in a way so as to bind specific analytes, then the changes in the mode structure can be used to measure analyte binding.

Some mode structure changes usable for the present techniques include a shift in the mode frequency, a change in the width of the resonance (or the Q of the cavity) and changes in the relative efficiency of mode coupling. One specific measurement technique for measuring the cavity Q is cavity ringdown, where the optical power of the input beam 214 is shut off and the decay of the evanescent signal 216 at a fixed location is measured to determine the decay time of the cavity and hence the quality factor Q. This technique can measure cavity Q as low as about $10^7$ and as high as about $10^{11}$. Another is sweeping a narrow linewidth laser across the mode structure to measure directly the mode linewidth to determine the Q and coupling efficiency. To some extent, a high Q WGM resonator may be thought as to provide an extremely long interaction path Act length in a very compact package. For Q of $10^9$, the photon residence time is ~300 ns, for an effective path length of 90 m, which can be obtained in a 300 $\mu$m diameter microsphere.

The resonator 201 in FIG. 2 may also be coupled to a control mechanism to actively control the dimension of the resonator 201. For example, a pressure may be applied to change the dimension of the resonator 201. The presence of the sample can change operating conditions of the resonator, such as the optical coupling efficiency in coupling energy to the resonator 201. The pressure applied the resonator 201 may be adjusted so that the operating conditions remain the same as prior to introduction of the sample. This change in the applied pressure can be measured to extract information of the sample.

Notably, the above measurements may be performed at any convenient laser wavelength, without tuning to any wavelength specific absorption. The evanescent wave is measured to detect the geometric, scattering, or absorbing changes at the surface as the desired analyte binds to the microsphere cavity. The the wave detects the change in index of refraction caused by the bound layer. Experiments have shown this to be sensitive; a microsphere sensor easily detected $10^{-2}$ of a monolayer of water on the surface of a sphere.

An optical sensor based on a WGM microresonator can be designed to respond to specific analytes by adding a surface coating on the exterior surface of the resonator that binds to a specific substance or analyte. This surface coating may alternatively formed on the interfacing surface of the optical coupler that provides the evanescent coupling, such as the angle-polished surface of the fiber tip in FIG. 3A, or the bottom surface of the prism in FIG. 3B. In yet another possibility, both the exterior surface of the resonator and the interfacing surface of the optical coupler may be coated with such a surface coating that binds a specific substance. Examples of such coating include but are not limited to, immunosensors, proteins, DNA, polysaccharides, metal complexes, molecularly imprinted polymers or polymers that swell when exposed to chemicals, or any other coating sensitive to presence of certain analytes. When the surface coating thickness is less than the evanescent decay length, it generally does not materially affect the cavity performance. Hence, such coating can be used to measure specified molecules or particles.

In the example of immunosensors, in which the resonator surface is coated with immobilized antibodies, a derivatized surface on the microcavity binds specifically to the antigen and makes a detectable change in the cavity mode structure as it shifts the cavity frequency and/or changes the cavity Q due to increased surface scattering or absorptive losses. Sensor specificity comes from the antibody-antigen reaction or surface coating-analyte reaction.

The sensor sensitivity may be increased through use of an absorbing molecule, for example, a fluorophore. Hence,,in a sandwich-type assay, a second reaction is performed in which a conjugated antibody-fluorophore pair binds to the previously bound antigen. If the fluorophore absorbed at the wavelength of the detection light, it would increase the WG photon losses and reduce the cavity Q significantly. In this implementation, the change of the Q is measured for detection. The fluorescence may not be specifically measured for detection although it could be used to provide another detection mechanism. Since the effective optical path is long, there is a concomitant increase in the fluorescence signal.

It is further contemplated that, multiple of WGM micro cavities may be used to form a detector array. In one implementation, each microcavity of the array can have a separate coating/reactive surface that is sensitive to a different analyte. Multiple analytes may be measured to provide for redundancy and blanks all in one sensor.

In the above measurements, the observed signal includes a temporal change in the whispering gallery mode spectrum. Such changes may include, but are not limited to, a shift of the mode structure, change of relative amplitudes of different modes and change in shape of specific resonances. The temporal shift of the mode structure is due to the temporal change in the geometry of the sensitive region which is located on the resonator, the coupler, or both. The geometry changes upon adsorption of analyte from solution thereby changing effective radius of the resonator in case of coated resonator or changing effective gap between resonator and coupler which is coated with a layer to bind a specific substance. The change of the radius of the resonator will be manifested in the shift of the mode structure in the frequency domain. The quality factor of particular resonance will not necessarily be changed. Therefore, tracking the shift of modes with time provides a sensitive measurement directly related to changes in the geometry of the resonator.

Figure 7:
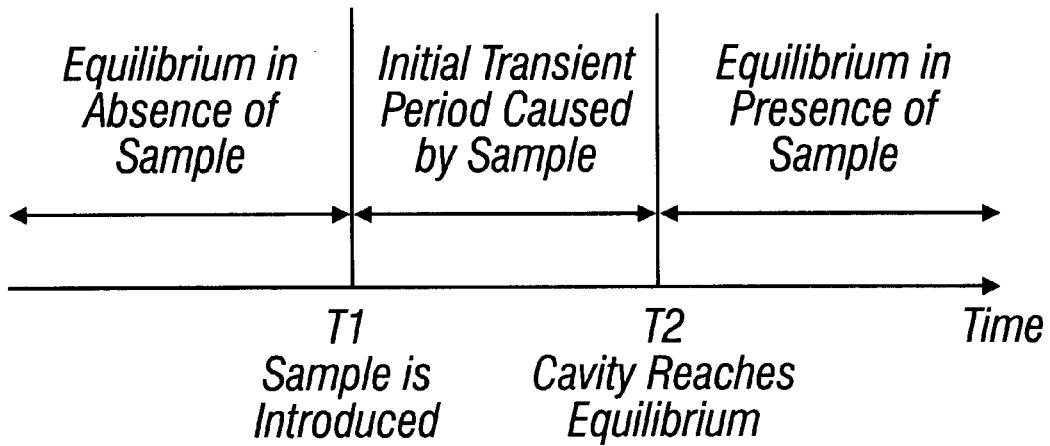
FIG. 7 shows three different periods associated with measurements in the system in FIG. 2.

The change in the measured signal due to the introduction of the sample may be measured to two different ways. FIG. 7 shows three different periods with respect to introducing the sample to the sensing WGM resonator at time T1. The first period is before the sample is introduced and the sensing WGM resonator reaches an equilibrium state in absence of the sample. The second period is an initial transient period between T1 and T2 at which the resonator reaches a different equilibrium state after the sample is introduced. The third period is after the time T2 where the resonator reaches the different equilibrium state. Referring back to FIG. 4, the two a different measured values of a selected characteristic property of the resonator may be respectively measured during the first and the third periods, such as the Q factor, the mode frequency, or the mode coupling efficiency. However, the two values may also be measured during the transient period when the resonator is in a non-equilibrium state due to the introduction of the sample.

Figure 8:
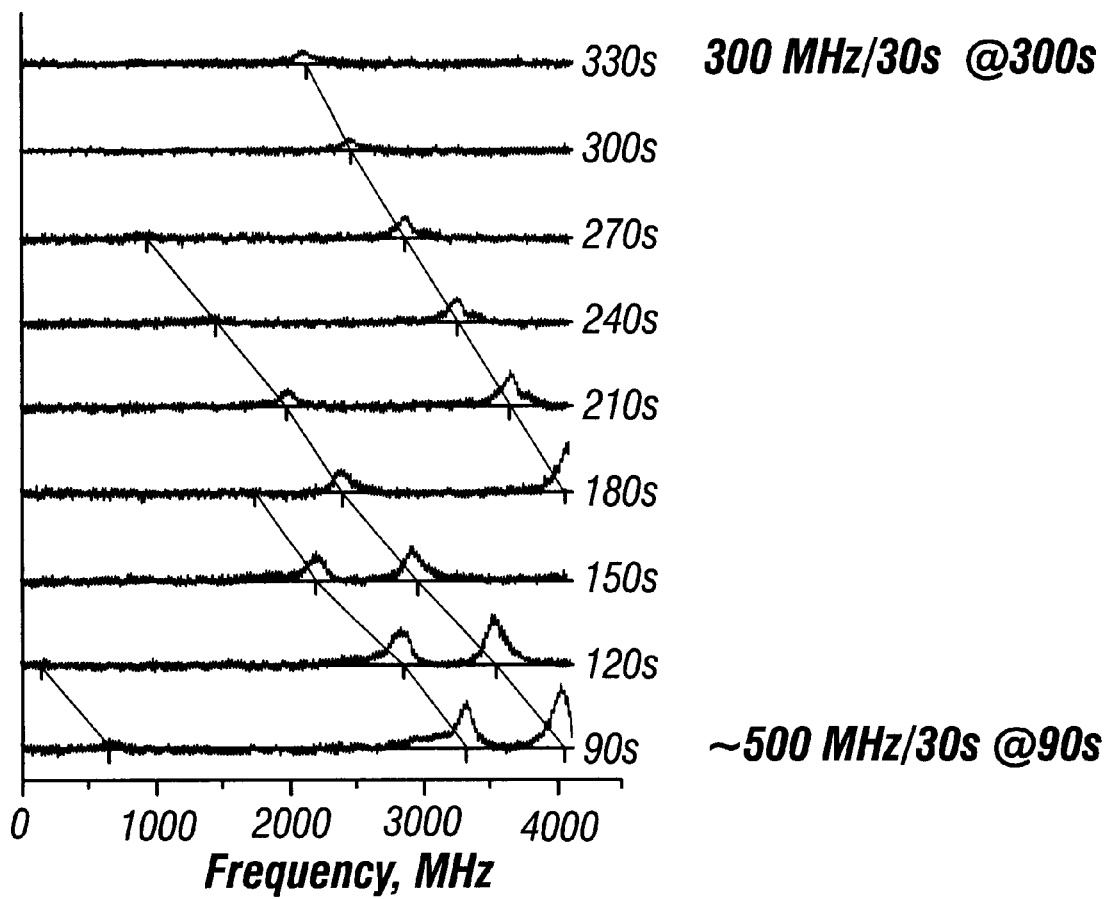
FIG. 8 shows measured frequency shift in WGM during a transient period after the sample is introduced to a microresonator in FIG. 2.

The temporal change of a selected characteristic property of the resonator, e.g., the mode frequency shift, is discovered to be more sensitive than the changes between values respectively measured in the two equilibrium states. FIG. 8 shows measured WGM mode spectra at different times during the transient period after an analyte is introduced to a microsphere cavity coated with Streptavidin. The measurements are taken from 90 s to 330 s by an interval of 30 s after the analyte is introduced. This frequency shift can then used to extract the information of the analyte. Notably, the oblate spheriodal microresonator may be preferred for such spectral measurements such as this one due to its large FSR and unambiguous resonator spectrum.

Measurements may be performed in all three periods illustrated in FIG. 7. The measurements taken in the two equilibrium periods may be used to obtain one measurement of the sample based on the method in FIG. 4. The measurements taken in the transient period may be used to obtain another measurement of the sample based on the method in FIG. 4.

Only a few embodiments are disclosed. However, it is understood that variations and enhancements may be made without departing from the spirit of and are intended to be encompassed by the following claims.

What is claimed is:

1. A device, comprising:
    an optical resonator to support a whispering gallery mode of an electromagnetic field;
    an optical coupler positioned adjacent to said optical resonator and having an interfacing surface to evanescently couple optical energy into or out of said optical resonator in said whispering gallery mode;
    a sample unit disposed relative to said optical resonator to supply a sample to a spatial region within a reach of and to interact with said electromagnetic field of said whispering gallery mode to produce a change in said optical energy in said optical resonator;
    an optical detector located relative to said optical coupler to receive an output from said optical coupler and measure said change during a transient period before said optical resonator reaches an equilibrium state in interaction with the sample; and
    a signal processor coupled to said optical detector to process an output from said optical detector to extract information on the sample.

2. The device as in claim 1, wherein said optical resonator includes a spherical portion of a sphere that comprises an equator.

3. The device as in claim 1, wherein said optical resonator has a non-spherical shape to provide a two-dimensional confinement.

4. The device as in claim 3, wherein said optical resonator is a spheroid.

5. The device as in claim 1, wherein said optical resonator has an exterior coated to bind a selected substance.

6. The device as in claim 1, wherein said interfacing surface of said optical coupler is coated to bind a selected substance.

7. A method, comprising:
    measuring a first value of a property of an output optical signal from an optical resonator that supports a whispering gallery mode in absence of a sample;
    measuring a second value of the property of the output optical signal from the optical resonator when the sample is present within a reach of the whispering gallery mode; and
    extracting information of the sample from a difference between the first and the second value.

8. The method as in claim 7, wherein the property includes a decay time of the optical resonator.

9. The method as in claim 7, wherein the property includes a frequency shift in a mode frequency of the whispering gallery mode.

10. The method as in claim 7, wherein the property includes a change in a line width of a resonance of the optical resonator.

11. The method as in claim 7, wherein the property includes a change in a mode coupling efficiency associated with the whispering gallery mode.

12. The method as in claim 7, wherein said first value is measured when said optical resonator is in an equilibrium state in absence of the sample, and said second value is measured when said optical resonator in another equilibrium state in presence of the sample.

13. The method as in claim 7, wherein said first and said second value are measured during a transient period when said optical resonator is in a non-equilibrium state due to an interaction with the sample.

14. A device, comprising:
    an optical resonator having a geometry of an oblate spheroid to support a whispering gallery mode;
    an optical coupler positioned adjacent to said optical resonator to evanescently couple optical energy into said optical resonator in said whispering gallery mode or out of said optical resonator to produce an output signal;

a sample unit disposed adjacent to said optical resonator to supply a sample to a spatial region within a reach of an electromagnetic field of said whispering gallery mode to interact with said electromagnetic field to produce a change in said output signal;

an optical detector located relative to said optical coupler to measure said change in said output signal; and a signal processor coupled to said optical detector to process an output from said optical detector to extract information on the sample.

15. The device as in claim 14, wherein said optical detector is configured to measure a frequency shift in said whispering gallery mode.

16. The device as in claim 14, wherein said optical detector is configured to measure a decay time of said optical resonator.

17. The device as in claim 14, wherein said optical detector is configured to measure a change in a linewidth of a resonance of said optical resonator.

18. The device as in claim 14, wherein said optical detector is configured to measure a change in a mode coupling efficiency associated with said whispering gallery mode.

19. The device as in claim 14, wherein said optical detector is configured to measure a change in a frequency shift in said whispering gallery mode during a transient period when said optical resonator is in a non-equilibrium state due to an interaction with the sample.

20. A device, comprising:

an optical resonator having a dielectric hollow shell with a thickness less than on wavelength of an optical signal and a medium filled in said hollow shell with a refractive index greater than a refractive index of said hollow shell, said optical resonator configured to support a whispering gallery mode;

an optical coupler positioned adjacent to said optical resonator and having an interfacing surface to evanescently couple said optical signal into said optical resonator in a whispering gallery mode or to couple energy out of said optical resonator to produce an output signal;

a sample unit coupled to said optical resonator to supply a sample into said medium within a reach of an electromagnetic field of said whispering gallery mode to interact with said electromagnetic field to produce a change in said output signal;

an optical detector positioned relative to said optical coupler to receive said output signal and to measure said change; and a signal processor coupled to said optical detector to process an output from said optical detector to extract information on the sample.

21. The device as in claim 20, wherein said optical resonator includes a spherical portion of a hollow sphere that comprises an equator.

22. The device as in claim 20, wherein said optical resonator is a hollow spheroid.

23. The device as in claim 20, wherein said optical resonator has an exterior coated to bind a selected substance.

24. The device as in claim 20, wherein said interfacing surface of said optical coupler is coated to bind a selected substance.

25. A method, comprising:

causing a measurement of a first value of a property of an output optical signal from an optical resonator that supports a whispering gallery mode in absence of a sample;

causing a measurement of a second value of the property of the output optical signal from the optical resonator when the sample is present within a reach of the whispering gallery mode; and causing a difference between the first and the second value to be processed to extract information of the sample.

26. The method as in claim 25, wherein said first value is measured when said optical resonator is in an equilibrium state in absence of the sample, and said second value is measured when said optical resonator in another equilibrium state in presence of the sample.

27. The method as in claim 25, wherein said first and said second value are measured during a transient period when said optical resonator is in a non-equilibrium state due to an interaction with the sample.

28. The method as in claim 27, wherein the property includes a frequency shift in a mode frequency of the whispering gallery mode.

* * * * *